(12) United States Patent
Batzer

(10) Patent No.: US 11,642,062 B2
(45) Date of Patent: May 9, 2023

(54) PRODUCTION OF ELECTRICAL CONTACT WITH SKIN

(71) Applicant: Ulrich Batzer, Buckenhof (DE)

(72) Inventor: Ulrich Batzer, Buckenhof (DE)

(73) Assignee: Siemens Healthcare GmbH, Erlangen (DE)

( * ) Notice: Subject to any disclaimer, the term of this patent is extended or adjusted under 35 U.S.C. 154(b) by 1634 days.

(21) Appl. No.: 15/066,848

(22) Filed: Mar. 10, 2016

(65) Prior Publication Data

US 2016/0262644 A1    Sep. 15, 2016

(30) Foreign Application Priority Data

Mar. 10, 2015 (DE) .......................... 102015204207.3

(51) Int. Cl.
*A61B 5/25* (2021.01)
*A61B 5/252* (2021.01)
*A61B 5/259* (2021.01)

(52) U.S. Cl.
CPC ................ *A61B 5/25* (2021.01); *A61B 5/252* (2021.01); *A61B 5/259* (2021.01)

(58) Field of Classification Search
CPC .............. A61B 5/0408; A61B 5/04082; A61B 5/04087; A61B 5/04085; A61B 5/0416; A61B 2562/22; A61B 2562/227; A61B 5/25; A61B 5/252; A61B 5/259; A61B 5/291; A61B 5/0022; A61B 5/0077; A61B 5/165; A61B 5/6898; A61B 5/721;
(Continued)

(56) References Cited

U.S. PATENT DOCUMENTS 3,995,644 A * 12/1976 Parsons ..................... A61N 1/05
607/116
4,232,930 A * 11/1980 Teti ........................ H01R 13/502
439/680
(Continued)

FOREIGN PATENT DOCUMENTS

AT        407486 B      3/2001
CH        662717 A5    10/1987
(Continued)

OTHER PUBLICATIONS

German office Action for related German Application No. 10 2015 204 207.3 dated Oct. 23, 2015, with English Translation.
(Continued)

*Primary Examiner* — Eun Hwa Kim
*Assistant Examiner* — Catherine Premraj
(74) *Attorney, Agent, or Firm* — Lempia Summerfield Katz LLC

(57) ABSTRACT

An electrode for producing electrical contact with skin is provided. The electrode includes a first electrical connection, a second electrical connection that is electrically insulated from the first electrical connection, and a skin contact. The skin contact has a first contact region that is electrically coupled to the first electrical connection, and a second contact region that is electrically insulated from the first contact region and is electrically coupled to the second electrical connection. The skin contact is configured to produce electrical contact between the skin and the skin contact when the electrode is in a state placed on the skin.

14 Claims, 5 Drawing Sheets

(58) Field of Classification Search
CPC ......... A61B 5/743; A61B 5/398; A61B 5/318;
A61B 5/389; A61B 5/01; A61B 5/1038;
A61B 5/1118; A61B 5/28; A61B 5/00;
A61B 5/24; A61B 5/308; A61B
2560/0242; A61B 2562/0204; A61B
2562/0219; A61B 2562/029; A61B
2562/043; G16H 40/67; G06F 19/00;
G06K 9/00671; G06K 9/209
USPC ..... 600/394; 439/600, 692, 696, 699.1, 498, 439/909
See application file for complete search history.

(56) References Cited

U.S. PATENT DOCUMENTS

| | | | |
|---|---|---|---|
| 4,375,219 A * | 3/1983 | Schmid | A61B 5/02438 600/393 |
| 4,490,005 A * | 12/1984 | Hovey | A61B 5/0408 439/592 |
| 4,660,562 A | 4/1987 | House, Sr. | |
| 5,114,424 A * | 5/1992 | Hagen | A61B 18/16 606/32 |
| 5,645,063 A * | 7/1997 | Straka, Jr. | A61B 5/04085 600/391 |
| 5,868,671 A | 2/1999 | Mahoney | |
| 6,285,899 B1 | 9/2001 | Ghaem et al. | |
| 7,215,989 B1 | 5/2007 | Burks | |
| 8,204,572 B1 | 6/2012 | Lang et al. | |
| 2003/0187490 A1 | 10/2003 | Gliner | |
| 2004/0019288 A1 * | 1/2004 | Kinast | A61B 5/0402 600/509 |
| 2006/0166563 A1 * | 7/2006 | Osypka | H01R 24/58 439/668 |
| 2007/0007973 A1 | 1/2007 | Matthiessen et al. | |
| 2008/0114220 A1 * | 5/2008 | Banet | A61B 5/14551 600/301 |
| 2009/0118790 A1 | 5/2009 | Van Herk | |
| 2010/0079156 A1 * | 4/2010 | Lee | A61B 5/0004 324/692 |
| 2010/0198044 A1 | 8/2010 | Gehman et al. | |
| 2011/0004090 A1 * | 1/2011 | Keightley | A61B 5/0478 600/383 |
| 2011/0204971 A1 | 8/2011 | Chang et al. | |
| 2012/0061257 A1 * | 3/2012 | Yu | A61B 5/02007 205/792 |
| 2012/0310053 A1 | 12/2012 | Henning et al. | |
| 2013/0231546 A1 * | 9/2013 | Choe | A61N 1/0408 600/391 |
| 2013/0289376 A1 | 10/2013 | Lang | |
| 2013/0338529 A1 * | 12/2013 | Ishijima | A61B 5/24 600/547 |
| 2014/0187063 A1 | 7/2014 | Selby et al. | |
| 2014/0378802 A1 * | 12/2014 | Livneh | A61B 5/04 600/372 |
| 2015/0173639 A1 * | 6/2015 | Ichida | A61B 5/291 600/397 |
| 2015/0374256 A1 | 12/2015 | Skrabal | |

FOREIGN PATENT DOCUMENTS

| | | |
|---|---|---|
| CN | 1196225 A | 10/1998 |
| CN | 1353592 A | 6/2002 |
| CN | 101237906 A | 8/2008 |
| CN | 101686808 A | 3/2010 |
| CN | 104144638 A | 11/2014 |
| DE | 2640133 A1 | 3/1978 |
| DE | 102005031751 A1 | 1/2007 |
| DE | 102006026677 A1 | 12/2007 |
| DE | 102011076885 A1 | 12/2012 |
| DE | 102013227203 A1 | 7/2014 |
| DE | 102014216757 A1 | 2/2016 |
| WO | WO2012092632 A1 | 7/2012 |
| WO | WO2014128237 A1 | 8/2014 |

OTHER PUBLICATIONS

M. Yelderman, B. Widrow, J. M. Cioffi, E. Hesler and J. A Leddy "ECG enhancement by adaptive cancellation of electrosurgical interference", IEEE Trans. Biomed. Eng., vol. BME-30, pp. 392-398 1983, http://www-isl.stanford.edu/~widrow/papers/1983ecgenhancement.pdf, 1983.

Chinese Office Action for related Chinese Application No. 201610292201.2 dated Jun. 26, 2018.

Ulrich Batzer "System and Method for Improving Common-Mode Noise Suppression" Siemens AG 2014. pp. 1-5 with English translation.

* cited by examiner

PRODUCTION OF ELECTRICAL CONTACT WITH SKIN

This application claims the benefit of DE 10 2015 204 207.3, filed on Mar. 10, 2015, which is hereby incorporated by reference in its entirety.

BACKGROUND

The present embodiments relate to an electrode for producing electrical contact with skin and a measuring apparatus for use with at least one electrode.

Although the present embodiments described below primarily in relation to adhesive electrodes, the present embodiments are not limited thereto. Instead, the present embodiments may be used with any type of electrode (e.g., suction electrodes or the like).

In modern medicine, a number of measuring instruments are used. By way of example, ECG systems or ECG appliances may be used in order to measure, for example, cardiac signals in the form of voltages or the like.

Usually, ECG applications for measuring the cardiac signals involve the use, depending on the instance of application, of at least three contacts between ECG appliance and the person whose cardiac signals are intended to be recorded.

The number of contacts may be up to ten contacts, however, in order to be able to analyze the potentials of the heart from different angles.

The minimum number of three contacts traces back to the circumstance that, in this minimal configuration, two contacts are used for differential measurement, and one contact is used as equipotential bonding. The contact for equipotential bonding is also referred to as the neutral electrode or right leg drive (RLD).

For better interference rejection, further contacts may also be used besides the measurement contacts and the neutral contact. By way of example, common mode interference may be measured and eliminated using two additional contacts. In addition to the RLD, equipotential bonding to ground may be performed by an additional contact. Training for common mode interference rejection methods may involve common mode interference being intentionally supplied to the system via a further contact.

In order to produce the contact between the ECG appliance and the person whose cardiac signals are intended to be recorded, electrodes that each provide an electrical contact may be used. This results in a high level of cabling complexity when a large number of contacts are to be provided. In addition, each electrode is to be attached to the skin of the person individually.

SUMMARY AND DESCRIPTION

The scope of the present invention is defined solely by the appended claims and is not affected to any degree by the statements within this summary.

The present embodiments may obviate one or more of the drawbacks or limitations in the related art. For example, simpler cabling of humans or animals using an ECG appliance is provided.

According to one or more of the present embodiments, the electrode for producing electrical contact with skin includes a first electrical connection (e.g., a female connector, a male connector, a base or the like) and a second electrical connection that is electrically insulated from the first electrical connection. The electrical connections may be used to make electrical contact with the electrode. In addition, the electrode has a skin contact that has a first contact region that is electrically coupled to the first electrical connection, and a second contact region that is electrically insulated from the first contact region and is electrically coupled to the second electrical connection. The skin contact is configured to produce electrical contact between the skin and the skin contact when the electrode is in a state placed on the skin.

An electrode may be any structure that may be attached to a surface (e.g., the skin of a living being) and may pick up electrical signals from the skin and convey the electrical signals (e.g., via a cable) to an ECG appliance.

The skin contact or the first contact region and the second contact region may be placed in contact with the skin and may have, for example, an electrically conductive contact gel, metal surfaces, surfaces made of another electrically conductive material, or the like.

The measuring apparatus according to one or more of the present embodiments may be, for example, an ECG appliance and may be used particularly with at least one electrode according to one or more of the present embodiments. The measuring apparatus has a number (e.g., one or more) of measurement connections that may be coupled to one of the electrodes. In addition, the measuring apparatus has a number of auxiliary connections that may be coupled to one of the electrodes.

The measurement connections and the auxiliary connections may be connected, for example, to cables, one end of which has a connection (e.g., a male connector or the like) that may be coupled to the electrical connections of the electrode. The male connector may be, for example, in the form of a pushbutton or the like. At their other end, the cables may have, for example, two separate male connectors that may be coupled to the measuring apparatus. Alternatively, the measuring apparatus and the cables may have a connecting system in which a male connector contains both the measurement connections and the auxiliary connections.

In the measuring apparatus, the measurement connections are used to receive signals from the electrodes that are used for the actual signal measurement (e.g., the recording of cardiac signals). The auxiliary connections are used to receive or output additional signals, such as the signal from the RLD electrode or the like, for example.

The insight on which one or more of the present embodiments is based is that the distance between the actual measurement electrodes of an ECG system and the auxiliary electrodes, such as the RLD electrode, does not need to be very great.

One or more of the present embodiments use this insight and provide a segmented electrode that has two contact regions that may make contact with the skin, for example, of a person. In addition, each of the contact regions has a respective separate electrical connection provided for the contact region that may be coupled, for example, via a cable or the like, to a measuring apparatus according to one or more of the present embodiments (e.g., an ECG appliance).

The segmentation of the electrode into multiple contact regions having multiple electrical connections results in a saving for the number of electrodes required.

By way of example, an ECG appliance that may be used, for example, in a computer tomograph for triggering purposes has two contacts for signal acquisition, one contact for equipotential bonding and a further contact for extended interference rejection methods. One or more of the present embodiments may be used to halve the number of electrodes in such a system from four to two.

One of the contacts for signal acquisition may in each case be arranged with one of the further contacts in an electrode according to one or more of the present embodiments.

The features of different exemplary embodiments may be combined to form new exemplary embodiments.

In order to be able to provide a compact electrode and to allow simple connection of the electrode, one embodiment may involve the first electrical connection and the second electrical connection being in essentially semicircular form and being arranged next to one another such that an essentially circular connection device is formed. "Essentially semicircular" or "essentially circular" is not just the circular shape. Rather, elliptical shapes and the like, for example, are also included. In one embodiment, the first electrical connection and the second electrical connection may also be rectangular and arranged next to one another such that the connection device assumes a likewise rectangular or square shape.

In further embodiments, the first electrical connection and/or the second electrical connection may be embodied as jack sockets and/or jack plugs. In yet further embodiments, the first electrical connection and/or the second electrical connection may be arranged in a female connector or a male connector of a multicontact connector system, such as, for example, a USB-like connector or the like.

If the electrode is intended to be used with conventional ECG appliances or coupled to an ECG appliance via conventional cables, then in one embodiment, the first electrical connection may be in essentially circular form. The second electrical connection may likewise be in essentially circular form. By way of example, the electrical connections may be in the form of pushbuttons or the like. In such an embodiment, the electrical connections may be at a distance from one another, so that each electrical contact may be connected separately to a cable.

In one embodiment, the first electrical connection and/or the second electrical connection may be arranged on the skin contact. This allows simple direct electrical coupling of the electrical connections to the respective contact region.

The electrode may be fixed to the skin in a simple manner if the electrode is in the form of an adhesive electrode. In one embodiment, the electrode has a support element that has, for example, an adhesive layer 9 on a side facing the skin in the state placed on the skin and has a recess with an inner contour that has the shape of an outer contour of the skin contact. The skin contact is arranged in the recess in the support element. The adhesive layer 9 is a layer of a material that adheres to skin and is suitable for keeping the electrode on the skin. In addition, in one embodiment, the skin contact or the individual contact regions have a contact gel that adheres strongly to the skin but that is easily deformable.

Alternatively, the electrode may also have a support element that has no adhesive layer 9. Such a support element may be used, for example, in an electrode that is in the form of a suction electrode or the like.

In order to decrease the influence of movements on the signals that are picked up by the electrode, one embodiment may involve the first electrical connection and/or the second electrical connection being arranged on the support element. In addition, the first electrical connection is coupled to the first contact region by a flexible, electrically conductive link (e.g., a wire or cable). The second electrical connection is coupled to the second contact region by a flexible, electrically conductive link (e.g., a wire or cable). Thus, a force effect on the cables that are coupled to the electrode may not be directly transferred to the skin contact.

In order to protect the electrode against radiated interference, one embodiment may include a shielding device that is arranged on a side of the skin contact that points away from the skin when the electrode is in a state placed on the skin. In this case, the shielding device may be produced from a conductive material that prevents capacitive coupling by electrical fields. The shielding device also includes a third electrical connection provided for the shielding device that is electrically coupled to the shielding device. The third electrical connection may be used to couple the shielding device, for example, to a further cable or to the shield of the cable or of the cables that are used in order to make contact with the first electrical connection and the second electrical connection.

In order to allow simple connection of the three electrical connections, one embodiment may involve the first electrical connection, the second electrical connection, and the third electrical connection each being essentially in circular sector form and being arranged next to one another such that an essentially circular connection device is formed. In this case, the sum of the angles of the circular sectors is less than 360 degrees. The split of the available surface over the individual electrical connections is variable in this case. By way of example, the circular sectors of the first and second electrical connections may have angles of approximately 135 degrees, while the circular sector of the third electrical connection may have 90 degrees. In one embodiment, the third electrical connection is arranged with the first and second electrical connections on the skin contact. Alternatively, the third electrical connection may be arranged with the first and second electrical connections on the support element. In addition, the first electrical connection and the second electrical connection may be arranged on the skin contact, and the third electrical connection may be arranged on the support element. In addition, the first electrical connection and the second electrical connection may be arranged on the skin contact, and the third electrical connection may be arranged on the support element.

For the purpose of simple evaluation of the signals that are provided by the electrodes according to one or more of the present embodiments, the measuring apparatus has, in one embodiment, a signal processing device having a number of measurement signal inputs and a number of auxiliary signal inputs that is configured to evaluate signals received via the measurement connections and/or the auxiliary connections.

Since it is often not possible to tell in advance which of the electrodes or which of the contact regions provides the most reliable measured values, one embodiment may have provision for a controllable switching device that is configured to controllably couple each of the measurement connections and/or each of the auxiliary connections to a prescribed measurement signal input or auxiliary signal input of the signal processing device. As a result, the signal from a contact region that is coupled to one of the auxiliary connections may, for example, be connected to a measurement connection, as required. This is advantageous, for example, when stronger signal levels are received via the auxiliary connection.

In order to establish which of the contact regions of the electrodes coupled to the measuring apparatus provides the best measurement results, one embodiment may have provision for a measuring device that is configured to measure a respective skin contact resistance for each of the measurement connections and each of the auxiliary connections when the electrode is in a state placed on the skin. The controllable switching device may then couple the measurement connections and/or auxiliary connections for which the measuring device has measured the lowest skin contact resistances to the measurement signal inputs of the signal processing device. Alternatively, the skin contact resistances may, for example, also be estimated. By way of example, an average signal strength that is received at the individual measurement connections and auxiliary connections may be ascertained. In this case, the connections having the highest signal levels denote the lowest skin contact resistance. In one embodiment, the cardiac signals (e.g., in the form of voltages; of differential voltages between two electrodes or contact regions) are measured using the electrodes or contact regions that have the lowest skin contact resistances.

For the purpose of simple measurement and exact determination of the skin contact resistance, one embodiment may involve the measuring device having at least one current source that is configured to supply a current at a prescribed current intensity to each of the measurement connections and each of the auxiliary connections. An evaluation device may take the current and the voltage drop produced by the current as a basis for computing the relevant skin contact resistance for each of the measurement connections and each of the auxiliary connections.

Since the measuring apparatus already contains a signal processing device, the evaluation device may be arranged in the signal processing device. By way of example, the evaluation device may be embodied as a program module or a function in the signal processing device.

The above refinements and developments may, where meaningful, be combined with one another, as desired. Further possible refinements, developments, and implementations also cover combinations not explicitly cited for features of the invention that are described above or below for the exemplary embodiments. For example, a person skilled in the art will also add individual aspects as improvements or additions to the respective basic form of the present invention in this case.

BRIEF DESCRIPTION OF THE DRAWINGS

Like components are provided with the same reference symbols in the various figures, in which.

DETAILED DESCRIPTION

Figure 1:
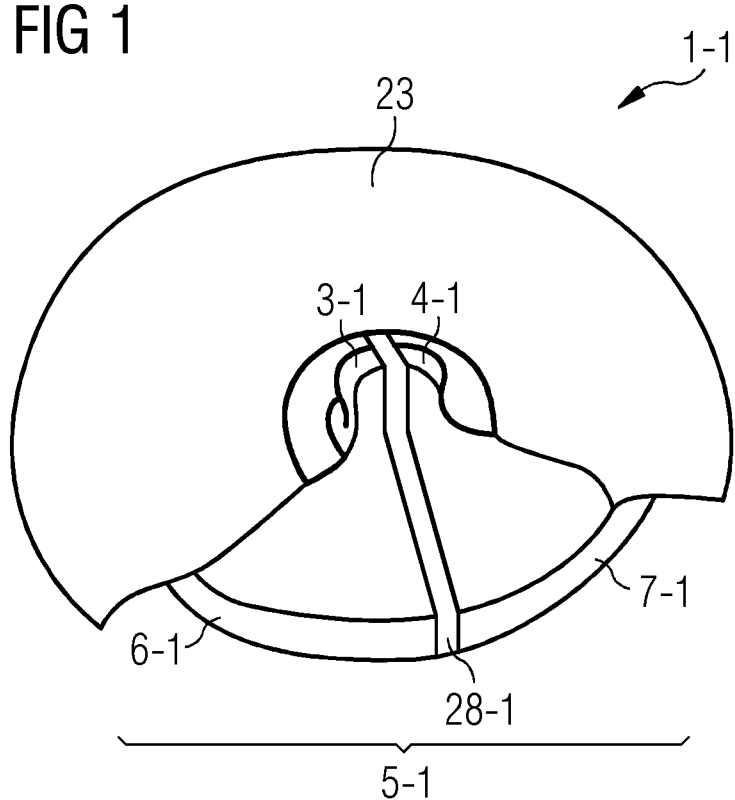
FIG. 1 shows a perspective view with a partial section through an embodiment of an electrode.

The electrode 1-1 in FIG. 1 includes two electrical connections 3-1 and 4-1 that are electrically insulated from one another. The two electrical connections 3-1 and 4-1 each form the half of a pushbutton. In a plan view, the two electrical connections 3-1 and 4-1 are each in semicircular form. The electrical connections 3-1 and 4-1 may be produced, for example, from an electrically conductive metal or another electrically conductive material.

The pushbutton may have a pressure contact (e.g., of a cable) pushed onto the pushbutton in order to make an electrical link between the cable and the first electrical connection 3-1 and the second electrical connection 4-1. The pressure contact may likewise have two segments or electrical contacts that correspond to the electrical connections 3-1 and 4-1.

Since the two electrical connections 3-1 and 4-1 are in semicircular form and the pushbutton is therefore round, a locking device that prevents the pressure contact from being able to rotate on the pushbutton (not shown in FIG. 1) may optionally be provided. In one embodiment, the locking device may include, for example, two simple bars that rise from the electrode 1-1 and between which a housing for the pushbutton is placed.

Alternatively, the shape of the electrical connections 3-1 and 4-1 may be in a form such that twisting of the pushbutton is prevented. By way of example, the electrical connections 3-1 and 4-1 may be oval, elliptical, square or the like.

Alternatively, the first electrical connection 3-1 and/or the second electrical connection 4-1 may be embodied as jack sockets and/or jack plugs. The first electrical connection 3-1 and/or the second electrical connection 4-1 may also be arranged in a female connector or a male connector of a multicontact connector system (e.g., a USB-like connector or the like).

In one embodiment, an adapter that has one end coupled to the electrical connections 3-1 and 4-1 of the electrode 1-1 and, at the other end, has two separate connections for conventional cables or connectors may also be provided.

The electrode 1-1 has, below the electrical connections 3-1 and 4-1, a skin contact 5-1 that has two contact regions 6-1 and 7-1 that are likewise electrically insulated from one another. The skin contact 5-1 is used to make the electrical contact between the skin (e.g., of a patient) and the electrical connections 3-1 and 4-1. The two contact regions 6-1 and 7-1 may have, for example, a contact gel, metal plates, or the like.

In order to electrically insulate the electrical connections 3-1 and 4-1 and also the contact regions 6-1 and 7-1 from one another, an insulation 28-1 is arranged in the electrode 1-1. In one embodiment, this may be, for example, a plastic bar made of an electrically nonconductive material. So as not to adversely affect wearing comfort, one embodiment may also involve the use of a foam made of an electrically nonconductive material or the like. In one embodiment, the insulation 28-1 may also have a nonconductive gel in the lower region supported on the skin, so that when the electrode 1-1 is worn on the skin, it is not possible to feel a difference between the contact regions 6-1, 7-2 and the insulation 28-1.

In FIG. 1, the contact regions 6-1 and 7-1 are in approximately circular form. This refinement is merely exemplary and, in other applications, may differ from the one shown. By way of example, the contact regions 6-1 and 7-1 may also be in oval, elliptical, rectangular or suchlike form.

An optional cover 23 is provided above the skin contact 5-1 in FIG. 1. The cover protects the contact regions 6-1 and 7-1 from touch. In addition, the electrode 1-1 may be combined with any device or way for fixing the electrode 1-1 to skin.

Figure 2:
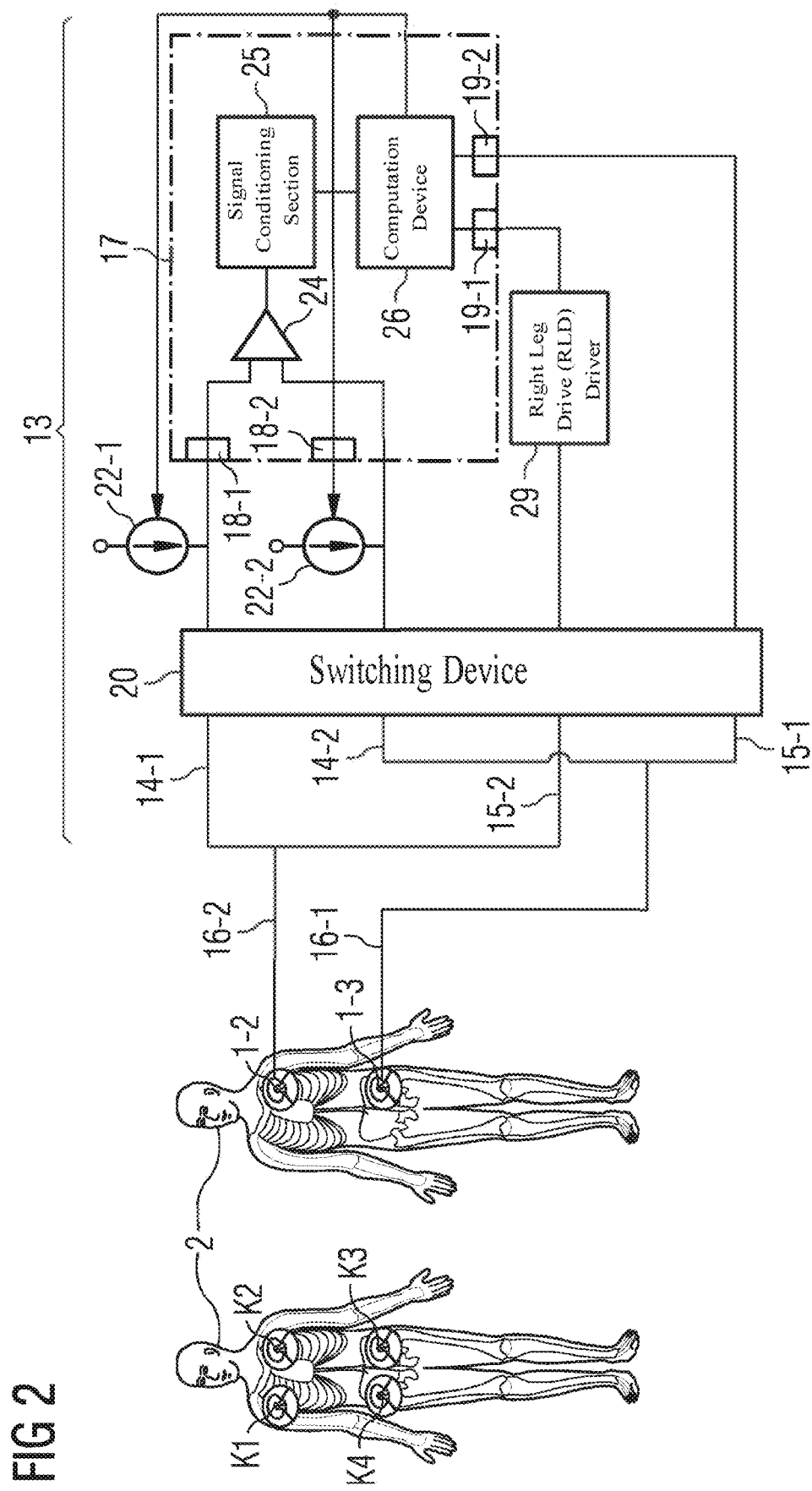
FIG. 2 shows a block diagram of an embodiment of a measuring apparatus.

FIG. 2 shows a measuring apparatus 13 that is coupled to electrodes 1-2 and 1-3, according to one or more of the present embodiments, that have been placed on the skin 2 of a person. To the left of the person, a second person is shown for comparison. The body of the second person has four conventional electrodes K1-K4 attached. The effort for attaching the electrodes 1-2 and 1-3 is halved in comparison with the known electrodes K1-K4.

The measuring apparatus 13 has two measurement connections 14-1, 14-2 and two auxiliary connections 15-1, 15-2 that are coupled to the electrodes 1-2, 1-3 via cables 16-1, 16-2. In this case, each cable 16-1, 16-2 is coupled to precisely one of the electrodes 1-2, 1-3, one of the measurement connections 14-1, 14-2, and one of the auxiliary connections 15-1, 15-2. The cables 16-1, 16-2 may have, for example, at least two signal lines or wires. In one embodiment, the cable is shielded (e.g., the signal lines or wires are encased by a common shield). Alternatively, the cables 16-1, 16-2 may have at least two signal lines or wires that are each shielded separately.

The measurement connections 14-1, 14-2 are used to transmit the actual measurement signals (e.g., cardiac signals) to a signal processing device 17 (e.g., a signal processor) of the measuring apparatus 13. By contrast, the auxiliary connections 15-1, 15-2 are used to transmit auxiliary signals from the electrodes 1-2, 1-3 to the signal processing device 17 or vice versa. The auxiliary signals are used for interference rejection, to improve signal quality or the like. Such a signal may be, for example, the RLD signal or a consciously produced interference signal for calibrating interference rejection algorithms.

The signal processing device 17 has two measurement signal inputs 18-1 and 18-2 that the signal processing device 17 uses to pick up the measurement signals from the measurement connections 14-1, 14-2. To pick up or output the auxiliary signals via the auxiliary connections 15-1, 15-2, the signal processing device 17 has two auxiliary signal inputs 19-1, 19-2.

To process the measurement signals, the signal processing device 17 has an amplifier 24 that, in one embodiment, may be, for example, an adjustable differential amplifier 24. The amplified signals are provided for a signal conditioning section 25 that conditions the amplified signals such that the amplified signals may be processed by a computation device 26 (e.g., a processor). In this case, the signal conditioning section 25 may be an analog, discrete digital signal conditioning section 25, or one implemented as a program, or the like.

The elements of the measuring apparatus 13 that have been shown hitherto in relation to FIG. 2 may, in one embodiment, be augmented by further useful elements.

To produce the RLD signal already mentioned above, the measuring apparatus 13 may have, for example, an RLD driver 29 that is arranged between the auxiliary signal input 19-1 and the auxiliary connection 15-2 of the measuring apparatus 13.

In addition, in one embodiment, a switching device 20 may be provided that, in FIG. 2, has the measurement connections 14-1, 14-2 and auxiliary connections 15-1, 15-2 of the measuring device 13.

The switching device 20 may also be referred to as a switching matrix 20 and is configured to controllably couple each of the measurement connections 14-1, 14-2 and each of the auxiliary connections 15-1, 15-2 to one of the measurement signal inputs 18-1 and 18-2 or auxiliary signal inputs 19-1, 19-2. The switching device 20 may have a number of switches (e.g., relays), semiconductor switches, or the like.

The switching device 20 may therefore be used to couple those connections, regardless of whether measurement connections 14-1, 14-2 or auxiliary connections 15-1, 15-2, of the measuring apparatus 13 have the best signal properties to the signal processing device 17. In such an embodiment with a switching device 20, the distinction between measurement connections 14-1, 14-2 and auxiliary connections 15-1, 15-2 may be foregone, since the difference is no longer significant.

The assignment of the individual measurement connections 14-1, 14-2 and auxiliary connections 15-1, 15-2 to the measurement signal inputs 18-1 and 18-2 or the auxiliary signal inputs 19-1, 19-2 may be made manually in one embodiment. For example, an operator control unit may be provided on the switching device 20.

Alternatively, the measuring apparatus 13 may be configured to determine the electrodes 1-2, 1-3 or the measuring connections 14-1, 14-2 or auxiliary connections 15-1, 15-2 that deliver the best suited measurement signals (e.g., the measurement signals having the greatest signal amplitudes) or have the lowest skin contact resistance.

By way of example, FIG. 2 shows two current sources 22-1, 22-2 that are coupled to the lines between the measurement connections 14-1, 14-2 and the signal processing device 17. Such current sources may also be provided for the auxiliary connections 15-1, 15-2.

In order to determine the skin contact resistance between the individual contact regions of the electrodes 1-2, 1-3 and the skin 2, the current sources 22-1, 22-1 may be actuated to supply a current having a prescribed current intensity to the respective contact regions of the electrodes 1-2, 1-3. Based on Ohm's law, U=R*I or R=U/I, the skin contact resistance may be determined from the prescribed current intensity and the voltage measured across the respective contact region.

In a further embodiment, the signal processing device 17 or the computation device 26 may, for example, be configured to use the signals acquired via the electrodes 1-2, 1-3 to estimate the contact regions having the lowest skin contact resistance. This may be accomplished, for example, using an average signal strength, with a lower signal level denoting a higher skin contact resistance and vice versa.

In one embodiment, just a single current source that may be coupled by the switching device 20 to all the connections 14-1, 14-2, 15-1 and 15-2 of the measuring apparatus 13 sequentially (e.g., in succession) may be provided.

By way of example, in one embodiment, the signal processing device 17 or the computation device 26 may actuate the switching device 20 such that the connections 14-1, 14-2, 15-1 and 15-2 having the lowest skin contact resistances are coupled to the measurement signal inputs 18-1, 18-2 of the signal processing device 17.

The number of measurement connections 14-1; 14-2, of auxiliary connections 15-1; 15-2, of measurement signal inputs 18-1, 18-2, etc. of the measuring apparatus 13 is used merely to illustrate the principles of the one or more of the present embodiments and, in other embodiments, may differ from that shown.

In addition, self-evident elements of the measuring apparatus 13 are shown in FIG. 2 (not represented), such as, for example, a display apparatus for displaying the ECG signals or an operator control unit, such as a keyboard or a touchscreen, for example. In addition, the measuring apparatus 13 may have, for example, interfaces for forwarding the captured ECG data.

FIGS. 3 to 7 show further possible embodiments of electrodes 1-4—1-8 according to one or more of the present embodiments, in each case in a plan view.

Figure 3:
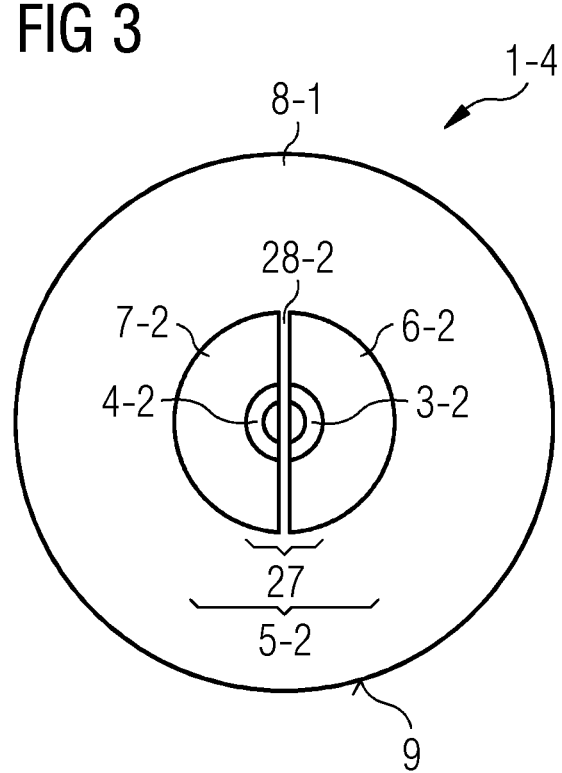
FIG. 3 shows a schematic plan view of an embodiment of an electrode.

The electrode 1-4 in FIG. 3 has a support element 8-1 that may be produced, for example, from a plastic or a textile material. Applied to the underside of the support element 8-1 (e.g., the side that is supported on the skin) is an adhesive layer 9 that may be used to stick the electrode 1-4 to skin.

In the center of the support element 8-1, the first contact region 6-2 and the second contact region 7-2 are shown. Each of the first contact region 6-2 and the second contact region 7-2 is in semicircular form and situated next to one another, so that the first contact region 6-2 and the second contact region 7-2 form a circular skin contact 5-2.

The first electrical connection 3-2 and the second electrical connection 4-2 are each arranged on the corresponding contact region 6-2, 7-2, so that the first electrical connection 3-2 and the second electrical connection 4-2 together form an approximately circular connection device 27. Arranged between the first electrical connection 3-2 and the second electrical connection 4-2 and between the first contact region 6-2 and the second contact region 7-2 is the insulation 28-2, as already described in relation to FIG. 1. The connection device 27 is, as described in relation to FIG. 1, configured such that, for example, a pushbutton may be fitted or pushed on.

Even though a pushbutton is shown as an exemplary embodiment of the electrical connections 3-2, 4-2, any suitable electrical connections 3-2, 4-2 may be used in further embodiments.

The electrode 1-4 in FIG. 1 is in the form of an adhesive electrode, as already illustrated above. In further embodiments, the electrode 1-4 and any other of the electrodes 1-1 to 1-8 shown in the figures may also be in a different form. By way of example, the electrodes 1-1 to 1-8 may also be in the form of suction electrodes or the like.

Figure 4:
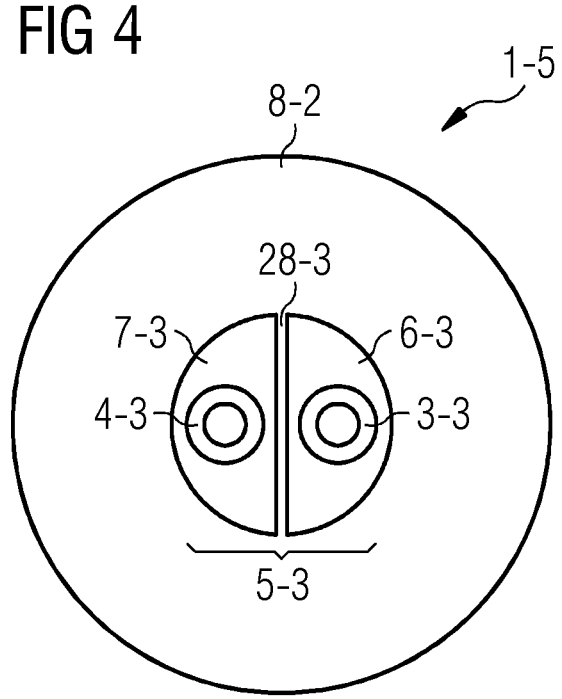
FIG. 4 shows a schematic plan view of an embodiment of an electrode.

The design of the electrode 1-5 in FIG. 4 is based on the design of the electrode 1-4 in FIG. 3. The difference between the electrode 1-5 and the electrode 1-4 is that the electrical connections 3-3 and 4-3 of the electrode 1-5 are in the form of separate connections 3-3 and 4-3 on the respective contact region 6-3 and 7-3. The two separate contact regions 6-3 and 7-3 therefore have contact made with them, for example, by two separate cables. Similar to the electrode 1-4 of FIG. 3, the electrode 1-5 of FIG. 4 includes a circular skin contact 5-3, a support element 8-2, and insulation 28-3 between the contact regions 6-3 and 7-3.

The embodiment in FIG. 4 is used to preserve backward compatibility with existing cables having standard single contacts.

Alternatively, an adapter cable may also be provided for the electrode 1-4 in FIG. 3. The adapter cable allows Y-splitting of the electrical connections 3-2, 4-2 over two separate contacts.

Figure 5:
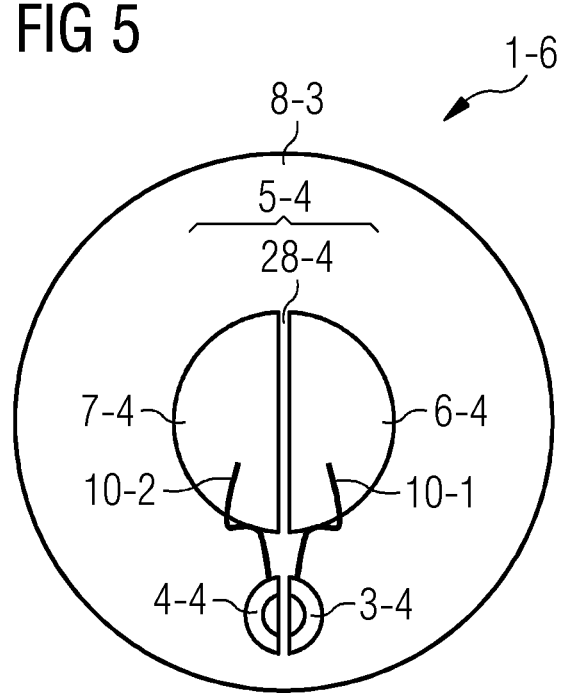
FIG. 5 shows a schematic plan view of an embodiment of an electrode.

FIG. 5 shows a further possible embodiment of an electrode 1-6. The electrode 1-6 or signal acquisition by the contact regions 6-4, 7-4 are more insensitive to mechanical faults. The electrode 1-6 of FIG. 5 includes a circular skin contact 5-4 and insulation 28-4 between the contact regions 6-4 and 7-4.

The design of the support element 8-3 and of the two contact regions 6-4, 7-4 is akin to the design for the electrode 1-4 in FIG. 3. However, the two electrical connections 3-4 and 4-4 are not arranged directly on the respective contact region 6-4, 7-4. Instead, the two electrical connections 3-4 and 4-4 are arranged on the support element 8-3 and coupled to the respective contact regions 6-4 and 7-4 via conductive links 10-1, 10-2. The conductive links 10-1, 10-2 used may be, for example, flexible conductors, such as wires, cables or flexible conductor tracks.

The mechanical decoupling of the electrical connections 3-4 and 4-4 from the two contact regions 6-4 and 7-4 results in a force effect on a cable that makes contact with the electrode 1-6 not being transferred directly to the contact regions 6-5, 7-4. Therefore, the influence of movements by the cable on the acquired signals is decreased.

Figure 6:
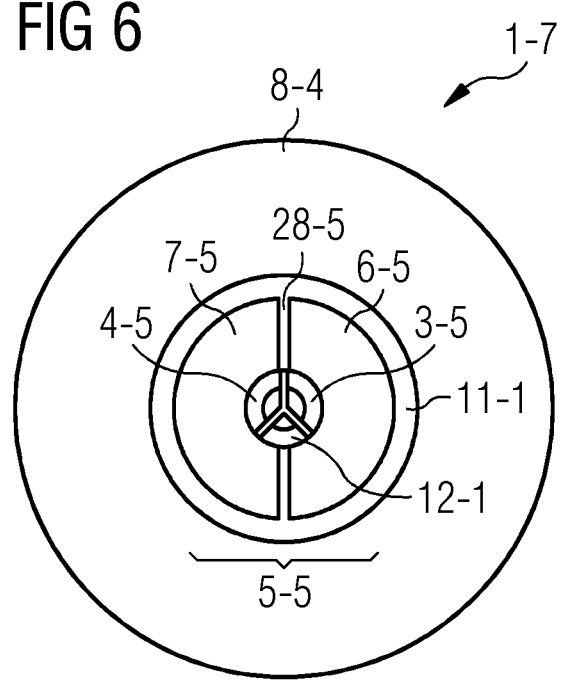
FIG. 6 shows a schematic plan view of an embodiment of an electrode.

FIG. 6 shows an electrode 1-7 that has a two-pole skin contact 5-5, like the electrode in FIG. 1. The electrode 1-7 of FIG. 6 includes a support element 8-4 and insulation 28-5 between the contact regions 6-5 and 7-5. The electrical connections 3-5 and 4-5 are also arranged in the center of the skin contact 5-5, so that a pushbutton is formed. However, the pushbutton has a third electrical connection 12-1. The first electrical connection 3-5 and the second electrical connection 4-5 are not in semicircular form, but rather have the shape of a circular sector with an angle of less than 180°. When the two electrical connections 4-5, 5-5 are put together, a gap in circular segment form is therefore produced. This gap contains the third electrical contact 12-1 in FIG. 6.

The third electrical contact 12-1 in FIG. 6 is used to make electrical contact with a shielding device 11-1 that protects the contact regions 6-5 and 7-5 against electrical radiated interference. The third electrical contact 12-1 may be coupled, for example, to the shield of a cable that makes contact with the electrode 1-7.

The shielding device 11-1 may be, for example, a layer of a conductive material that shields the contact regions 6-5 and 7-5 against electrical fields. This allows effective prevention of capacitive coupling that could otherwise lead to interference in the acquired signals.

If the shielding device 11-1 is connected to the shield of the cable and makes contact with the electrode 1-7 and the cable has a shielded electrode clip, which provides that even in the electrode clip or connector that is placed onto the pushbutton the electrical lines are shielded, then any interference injection in the electrode region is prevented in this manner.

Figure 7:
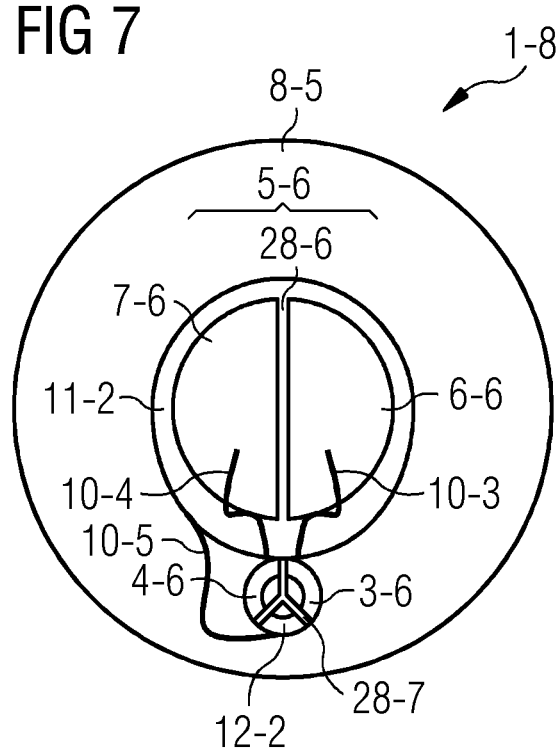
FIG. 7 shows a schematic plan view of an embodiment of an electrode.

The electrode 1-8 in FIG. 7 combines the properties of the electrodes 1-6 in FIG. 5 and electrodes 1-7 in FIG. 6. Similar to the electrodes 1-6 of FIGS. 5 and 1-6 of FIG. 6, the electrode 1-8 of FIG. 7 includes a circular skin contact 5-6 and insulation 28-6 between the contact regions 6-6 and 7-6. The contact regions 6-6 and 7-6 have a shielding device 11-2 provided above the contact regions 6-6 and 7-6, as in FIG. 6. In addition, the three electrical connections 3-6, 4-6 and 12-2 separated by insulation 28-7 are arranged on the support element 8-5 of the electrode 1-8, however, and coupled to the contact regions 6-6 and 7-6 or the shielding device 11-2 via flexible electrically conductive links 10-3 and 10-4, or 10-5, respectively.

In order not to adversely affect the reduction of movement influences by dint of the decoupling of the electrical connections 3-6, 4-6 and 12-2 from the contact regions 3-6, 4-6 and the shielding device 11-2 by dint of the shielding device 11-2, one embodiment may involve the shielding device 11-2 being permanently coupled to the support element 8-5 and loosely coupled to the contact regions 6-6, 7-6 or being permanently coupled to the contact regions 6-6, 7-6 and loosely coupled to the support element 8-5.

In FIGS. 1, and 3 to 7, the electrodes 1-1, 1-4-1-8 each have an approximately circular outer contour. This contour is intended to be one of many possible exemplary embodiments. By way of example, the electrodes may also have an oval, elliptical, rectangular or irregular outer contour.

The electrodes and measuring apparatuses described in detail above are merely exemplary embodiments that may be modified by a person skilled in the art in a wide variety of ways without departing from the scope of the invention. In addition, the use of the indefinite article "a" or "an" does not preclude the relevant features from also being present multiple times. Similarly, elements of the present invention that are presented as single units are not precluded from consisting of multiple interacting subcomponents that may also be physically distributed.

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. An electrode for producing electrical contact with skin, the electrode comprising: a first electrical connection; a second electrical connection that is electrically insulated from the first electrical connection; a skin contact comprising a first contact region and a second contact region, the first contact region being electrically coupled to the first electrical connection, the second contact region being directly adjacent to and electrically insulated from the first contact region and being electrically coupled to the second electrical connection; and a support element comprising: an adhesive layer on a side of the support element configured to face the skin when the electrode is configured to be in a state placed on the skin; and a recess portion with an inner contour having a shape of an outer contour of the skin contact, wherein the skin contact is arranged in the recess in the support element, wherein the skin contact is configured to produce electrical contact between the skin and the skin contact when the electrode is configured to be in the state placed on the skin, wherein the first electrical connection, the second electrical connection, or the first electrical connection and the second electrical connection are arranged on a portion of the support element separate from the recess portion, wherein the first electrical connection is coupled to the first contact region by a first flexible, electrically conductive link, wherein the second electrical connection is coupled to the second contact region by a second flexible, electrically conductive link, and wherein the first electrical connection and the second electrical connection are in essentially semicircular form and are arranged next to one another such that an essentially circular connection device is formed.

2. The electrode of claim 1, wherein, when the electrode is configured to be in the state placed on the skin, the support element is configured to be disposed on a surface of the skin, such that the support element is configured to be disposed between the surface of the skin and the first electrical connection, the second electrical connection, or the first electrical connection and the second electrical connection, in a direction away from and substantially perpendicular to the surface of the skin.

3. The electrode of claim 1, wherein the first flexible, electrically conductive link comprises a wire or a cable, and wherein the second flexible, electrically conductive link comprises a wire or a cable.

4. The electrode of claim 1, further comprising: a shielding device that is arranged on a side of the skin contact that is configured to point away from the skin when the electrode is configured to be in the state placed on the skin; and a third electrical connection that is electrically coupled to the shielding device, wherein the first electrical connection, the second electrical connection, and the third electrical connection are each essentially in circular sector form and are arranged next to one another such that an essentially circular connection device is formed.

5. A measuring, apparatus comprising: at least one electrode configured to produce electrical contact with the skin, an electrode of the at least one electrode comprising: a first electrical connection; a second electrical connection that is electrically insulated from the first electrical connection; a skin contact comprising a first contact region and a second contact region, the first contact region being electrically coupled to the first electrical connection, the second contact region being directly adjacent to and electrically insulated from the first contact region and being electrically coupled to the second electrical connection; and a support element comprising an adhesive layer on a side of the support element configured to face the skin when the electrode is configured to be in a state placed on the skin and a recess portion with an inner contour having a shape of an outer contour of the skin contact, wherein the skin contact is arranged in the recess in the support element, wherein the skin contact is configured to produce electrical contact between the skin and the skin contact when the electrode is configured to be in the state placed on the skin, wherein the first electrical connection, the second electrical connection, or the first electrical connection and the second electrical connection are arranged on a portion of the support element separate from the recess portion, wherein the first electrical connection is coupled to the first contact region by a first flexible, electrically conductive link, wherein the second electrical connection is coupled to the second contact region by a second flexible, electrically conductive link, and wherein the first electrical connection and the second electrical connection are in essentially semicircular form and are arranged next to one another such that an essentially circular connection device is formed; a plurality of measurement connections that are coupleable to one electrode of the at least one electrode; and a plurality of auxiliary connections that are coupleable to one electrode of the at least one electrode.

6. The measuring apparatus of claim 5, wherein the measuring apparatus is an ECG appliance and wherein the electrode of the at least one electrode is configured to pick up electrical signals from the skin and convey the electrical signals to the ECG appliance.

7. The measuring apparatus of claim 5, further comprising:
a signal processor comprising a plurality of measurement signal inputs and a plurality of auxiliary signal inputs, the signal processor being configured to evaluate signals received via the plurality of measurement connections, the plurality of auxiliary connections, or a combination thereof; and
a controllable switching device configured to controllably couple each measurement connection of the plurality of measurement connections, each auxiliary connection of the plurality of auxiliary connections, or a combination thereof to a prescribed measurement signal input of the plurality of measurement signal inputs or a prescribed auxiliary signal input of the plurality of auxiliary signal inputs of the signal processor.

8. The measuring apparatus of claim 7, further comprising: a measuring device configured to measure a respective skin contact resistance for each measurement connection of the plurality of measurement connections and each auxiliary connection of the plurality of auxiliary connections when the electrode is configured to be in the state placed on the skin, wherein the controllable switching device is configured to couple the measurement connections, auxiliary connections, or measurement connections and auxiliary connections for which the measuring device measures the lowest skin contact resistances to the measurement signal inputs of the signal processor.

9. The measuring apparatus of claim 8, wherein the measuring device comprises at least one current source that is configured to supply a current at a prescribed current intensity to each measurement connection of the plurality of measurement connections and each auxiliary connection of the plurality of auxiliary connections, and wherein the measuring device comprises an evaluation device configured to take a current and a voltage drop produced by the current as a basis for recording the relevant skin contact resistance for each measurement connection of the plurality of measurement connections and each auxiliary connection of the plurality of auxiliary connections.

10. The measuring apparatus of claim 9, wherein the evaluation device is arranged in the signal processor.

11. A method for using an electrode, the method comprising: measuring first ECG signals with a first contact region of a skin contact of the electrode configured to be in electrical contact with skin; measuring second ECG signals with a second contact region of a skin contact of the electrode configured to be in electrical contact with the skin, the second contact region being electrically insulated from the first contact region; communicating the first ECG signals with a first electrical connection, the first contact region being electrically coupled to the first electrical connection; and communicating the second ECG signals with a second electrical connection that is electrically insulated from the first electrical connection, the second contact region being directly adjacent to and electrically insulated from the first contact region and being electrically coupled to the second electrical connection; wherein the electrode comprises a support element comprising: an adhesive layer on a side of the support element configured to face the skin when the electrode is configured to be in a state placed on the skin; and a recess portion with an inner contour having a shape of an outer contour of the skin contact, wherein the skin contact is arranged in the recess in the support element, wherein the skin contact is configured to produce electrical contact between the skin and the skin contact when the electrode is configured to be in the state placed on the skin, wherein the first electrical connection, the second electrical connection, or the first electrical connection and the second electrical connection are arranged on a portion of the support element separate from the recess portion; wherein the first electrical connection is coupled to the first contact region by a first flexible, electrically conductive link, wherein the second electrical connection is coupled to the second contact region by a second flexible, electrically conductive link, and wherein the first electrical connection and the second electrical connection are in essentially semicircular form and are arranged next to one another such that an essentially circular connection device is formed.

12. The electrode of claim 1, wherein the first contact region and the second contact region are in essentially semicircular form and are arranged next to one another such that an essentially circular skin contact is formed.

13. The electrode of claim 1, wherein the first flexible, electrically conductive link is coupled to the first electrical connection only at a first end of the first flexible, electrically conductive link and coupled to the first contact region only at a second end of the first flexible, electrically conductive link, such that the first flexible, electrically conductive link is moveable between the first end and the second end independently of the first electrical connection, the second electrical connection, the skin contact, and the support element.

14. The measuring apparatus of claim 5, wherein the first flexible, electrically conductive link is coupled to the first electrical connection only at a first end of the first flexible, electrically conductive link and coupled to the first contact region only at a second end of the first flexible, electrically conductive link, such that the first flexible, electrically conductive link is moveable between the first end and the second end independently of the first electrical connection, the second electrical connection, the skin contact, and the support element.

* * * * *